United States Patent

Ballou et al.

[11] Patent Number: 6,071,308
[45] Date of Patent: Jun. 6, 2000

[54] FLEXIBLE METAL WIRE STENT

[75] Inventors: Kurt Ballou, Andover, Mass.; George T. Roberts, Mountain Lakes, N.J.; Kristian J. DiMatteo, Maynard; Adrian C. Ravenscroft, Milton, both of Mass.

[73] Assignee: Boston Scientific Corporation, Natick, Mass.

[21] Appl. No.: 08/942,162

[22] Filed: Oct. 1, 1997

[51] Int. Cl.[7] .............................. A61F 2/06; A61M 29/00
[52] U.S. Cl. ...................... 623/1.15; 623/1.16; 623/1.18; 606/198
[58] Field of Search ................... 623/1, 11, 12; 606/198

[56] References Cited

U.S. PATENT DOCUMENTS

| | | | |
|---|---|---|---|
| D. 380,266 | 6/1997 | Boatman et al. | D24/155 |
| D. 380,831 | 7/1997 | Kavteladze et al. | D24/155 |
| 5,102,417 | 4/1992 | Palmaz | 606/195 |
| 5,104,404 | 4/1992 | Wolff | 628/1 |
| 5,135,536 | 8/1992 | Hillstead | 606/195 |
| 5,195,984 | 3/1993 | Schatz | 606/195 |
| 5,290,304 | 3/1994 | Inoue | 606/191 |
| 5,354,308 | 10/1994 | Simon et al. | 606/198 |
| 5,395,390 | 3/1995 | Simon | 606/198 |
| 5,421,955 | 6/1995 | Lau et al. | 216/48 |
| 5,449,373 | 9/1995 | Pinchasik et al. | 606/198 |
| 5,466,242 | 11/1995 | Mori | 606/198 |
| 5,514,178 | 5/1996 | Torchio | 623/12 |
| 5,540,712 | 7/1996 | Kleshinski et al. | 606/198 |
| 5,545,210 | 8/1996 | Hess et al. | 623/1 |
| 5,591,197 | 1/1997 | Orth et al. | 606/198 |
| 5,643,339 | 7/1997 | Kvateladze et al. | 623/1 |
| 5,649,952 | 7/1997 | Lam | 606/198 |
| 5,653,727 | 8/1997 | Wiktor | 606/195 |
| 5,683,411 | 11/1997 | Kavteladze et al. | 606/200 |
| 5,695,516 | 12/1997 | Fischell et al. | 606/194 |

(List continued on next page.)

FOREIGN PATENT DOCUMENTS

| | | |
|---|---|---|
| 0 335 341 A1 | 10/1989 | European Pat. Off. . |
| 0 421 729 A2 | 4/1991 | European Pat. Off. . |
| 0 606 165 A1 | 7/1994 | European Pat. Off. . |
| 0 688 545 A1 | 12/1995 | European Pat. Off. . |
| 40 22 956 A1 | 2/1992 | Germany . |
| WO 9531945 A1 | 11/1995 | WIPO . |
| WO 96/33671 | 10/1996 | WIPO . |
| WO 96/39102 | 12/1996 | WIPO . |
| WO 96/41590 | 12/1996 | WIPO . |

(List continued on next page.)

OTHER PUBLICATIONS

The American Heritage Dictionary of the English Language, p. 1469, 1976.

"Experimental Intrahepatic Portacaval Anastomosis: Use of Expandable Gianurco Stents" by Josef Roseh, M. D.. in *Radiology*, Feb., 1987, pp. 481–485.

"Stenosis of the Vena Cava: Preliminary Assessment of Treatment with Expandable Metallic Stents" by Chusilp Charnsangaveg, M.D. et al. in *Radiology*. vol. 121, No. 2, Feb., 1987, pp. 295–298.

"Expandable Intraluminal Graft: A Preliminary Study" by Julio Palmaz et al, in *Radiology*, Jul. 1985, pp. 73–77.

"Radiological Follow–Up of Transluminally Inserted Vascular Endoprostheses: An Experimental Study Using Expanding Spirals" by D. Mass et al, *Radiology*, Sep. 1984, pp. 559–663.

(List continued on next page.)

*Primary Examiner*—David H. Willse
*Assistant Examiner*—Choon P. Koh
*Attorney, Agent, or Firm*—Vidas, Arrett & Steinkraus, P.A.

[57] ABSTRACT

A self-expanding metal wire stent made of shape memory alloy such as nitinol in which a plurality of spaced sections of closed cells are interconnected by straight sections of wire which may be parallel to the longitudinal axis of the stent or may be disposed angularly with respect thereto.

23 Claims, 6 Drawing Sheets

U.S. PATENT DOCUMENTS

| | | | |
|---|---|---|---|
| 5,697,971 | 12/1997 | Fischell et al. | 623/1 |
| 5,702,419 | 12/1997 | Berry et al. | 606/198 |
| 5,725,572 | 3/1998 | Lam et al. | 623/1 |
| 5,735,893 | 4/1998 | Lau et al. | 623/1 |
| 5,800,519 | 9/1998 | Sandock | 623/1 |
| 5,879,381 | 3/1999 | Moriuchi et al. | 623/1 |
| 5,902,232 | 5/1999 | Schatz | 623/1 |

FOREIGN PATENT DOCUMENTS

| | | |
|---|---|---|
| 97/09945 | 3/1997 | WIPO . |
| 97/14375 | 4/1997 | WIPO . |
| WO 97/32543 | 9/1997 | WIPO . |
| WO 97/32544 | 9/1997 | WIPO . |
| WO 97/33534 | 9/1997 | WIPO . |
| WO 97/41803 | 11/1997 | WIPO . |
| WO 98/05270 | 1/1998 | WIPO . |
| 98/07386 | 2/1998 | WIPO . |
| 98/18405 | 5/1998 | WIPO . |
| WO 98/37833 | 9/1998 | WIPO . |

OTHER PUBLICATIONS

"Gianturco Expandable Wire Stent In the Treatment of Superior Vena Cava Syndrome Recurring After Maximum–Tolerance Radiation" by Josef Roseh, M.D., et al, in *Cancer*, Sep. 15, 1987, vol. 60, pp. 1239–1246.

"Tracheobronchial Tree: Expandable Metallic Stents Used in Experimental and Clinical Applications" by Michael J. Wallace et al. vol. 158, No. 2, Radiology, Feb. 1986, pp. 309–312.

"Flexible Balloon–Expanded Stent For Small Vessels" by Gerard Duprat. Jr.. et al, Radiology, Jan. 1987.

"Elastic Characteristics of the Self–Expanding Metallic Stents" by B. G. Fallone, Ph.D., *Investigative Radiology*, May 1988, vol. 23, pp. 370–376.

"Percutaneous Endovascular Graft: Experimental Evaluation" by David Lawrence, Jr., M.D., et al, in *Radiology*, May 1987, pp. 357–360.

"Modified Gianturco Expandable Wire Stents In Experimental and Clinical Use" by J. Rosch et al in *CIRSE*, Porto Cervo, Sardinio, May 25–29, 1996.

Relocatable Ginaturco Expandable Metallic Stents, by Toshiyuki Irie, MD, et al., *Radiology*, 1991: 178:575–578.

PCT Search Report with a date of mailing of Jan. 15, 1999.

6,071,308

FLEXIBLE METAL WIRE STENT

BACKGROUND OF THE INVENTION

This invention relates to stents and is directed more particularly to a self-expanding, generally cylindrical stent preferably made of a shape memory alloy such as Nitinol.

Specifically, it is directed to an improved version of the type of stents described in U.S. Pat. No. 5,354,308 to Simon et al. and U.S. Pat. No. 5,540,712 to Kleshinski et al. The entire contents of these patents is incorporated herein by reference.

The stents of these patents are adapted to assume one configuration in which the stent is expanded and another configuration in which the stent is in a reduced size for delivery by catheter. The stent may be laminated within an elastomeric sleeve.

It has been deemed desirable to provide stents of this kind in elongated versions. Such elongated versions require additional flexibility over the length of the stent.

SUMMARY OF THE INVENTION

It is therefore, an object of the invention to provide stents of the foregoing type in which a plurality of radial sections or segments made up of the cells comprise the body of the stent the segments being interconnected by a single wire or one pair of adjacent sections of the wire which act as bridges, the straight connector sections being longitudinally aligned with the longitudinal dimension of the stent body or at an angle thereto. Such connector sections have been found to provide requisite flexibility in elongated versions of these types of stents both for delivery and implantation.

DETAILED DESCRIPTION OF THE PREFERRED EMBODIMENTS OF THE INVENTION

In the Figures similar numbers are used throughout to indicate similar elements.

Figure 1:
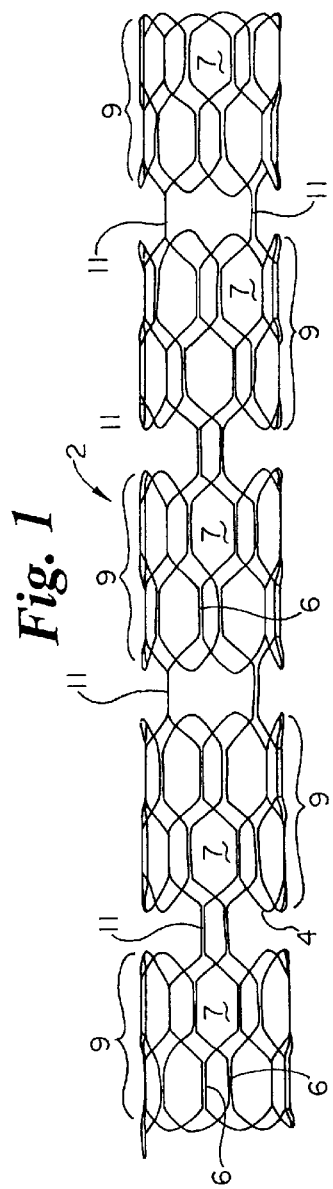
FIG. 1 is a view of one form a stent embodiment of the invention including two bridging sections between cell segments.
Figure 2:
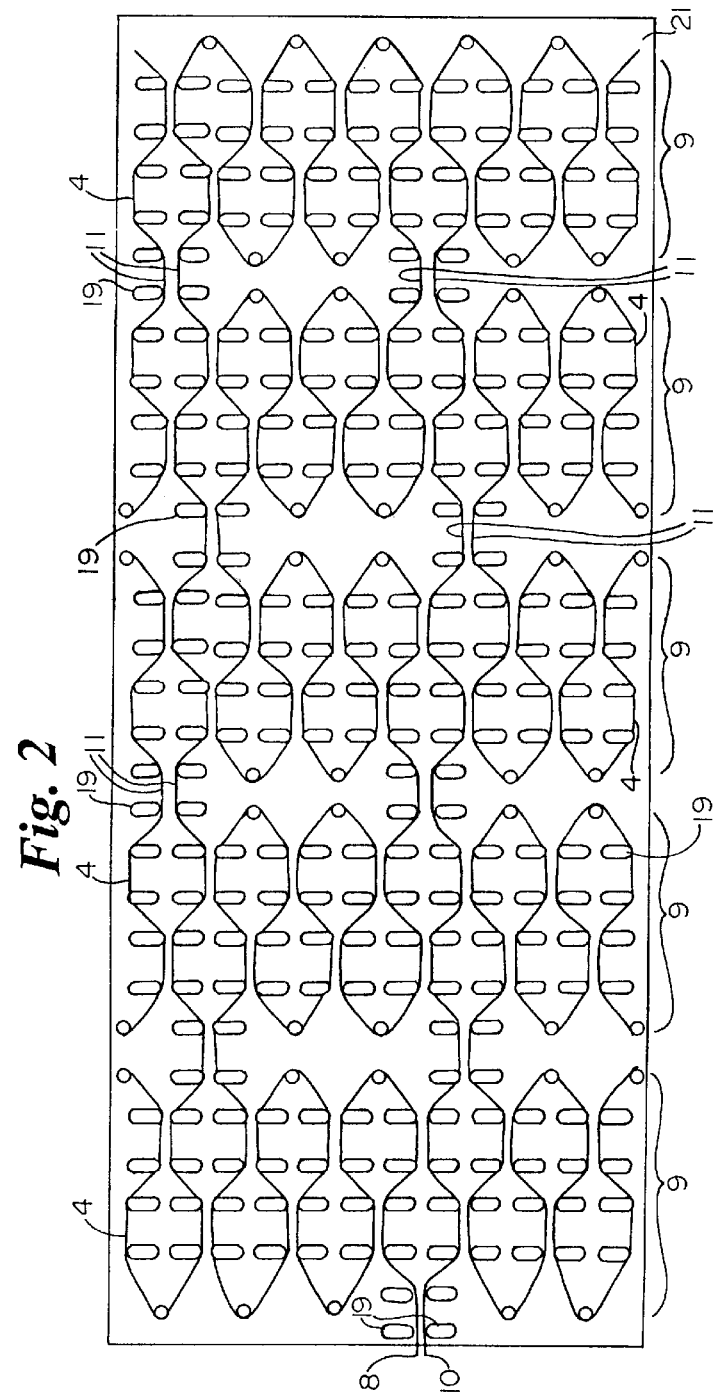
FIG. 2 is a view in flat projection that is a representation in planar view of a mandrel surface with up-standing pins for guiding the placement of a wire (wire winding pattern) in forming a stent of the invention of the type shown in FIG. 1 having two bridging sections between cell segments.
Figure 3:
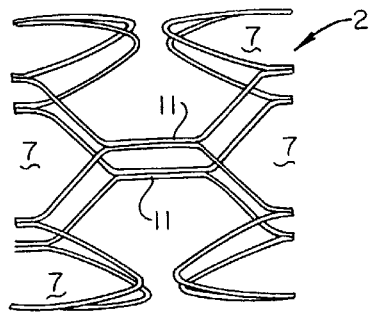
FIG. 3 is a close-up detail view of a portion of the two bridge stent arrangement of FIGS. 1 and 2.

Referring to FIGS. 1–3, it will be seen that one stent embodiment includes a skeletal frame generally indicated at 2, formed from a single wire 4. The frame is in the form of a hollow cylinder as can be seen in the Figures, the front surface being shown in detail while the rear surface is in shadow. Other hollow cross-sectional shapes may be used. The wire 4 includes a plurality of abutting straight portions 6 which are joined to each other, as by welding, to form closed cell configurations 7 which make up spaced sections or cell segments 9 to form the cylindrical body of the stent when connected together by bridging sections 11. In FIGS. 1–3, the stent is shown in a first condition in which the frame is expanded and relatively rigid.

Spaced cell sections or segments 9 are each interconnected by two bridging sections, each consisting of one pair of straight bridging sections 11 of wire 4 which are adjacent to each other and longitudinally aligned with respect to the longitudinal dimension of the stent body portion 9. Straight sections 11 function as connector members to interconnect cell segments 9 and to provide flexibility and spacing therebetween.

FIG. 2 shows the winding pattern of wire 4 in projection on the upstanding pins 19 of cylindrical mandrel 21, also shown in flattened projection. The winding pattern shown provides the desirable stent configuration of FIG. 1 which results in an elongated stent of improved flexibility.

In FIG. 1 the stent is shown in a first condition in which the frame 2 is expanded and substantially tubular in configuration. Ends 8, 10 of the single wire 4 making up the stent are disposed at one end of the stent as can be seen in FIG. 2. These ends are preferably welded together. The abutting and elongated straight portions 6 and 11 of wire 4 facilitate the use of strong elongated welds to securely join wire portions 6 together and 11 together. Preferably, welds of the type disclosed in co-pending U.S. application Ser. No. 08/735,031 will be used for this purpose. The content of that application is incorporated herein by reference. Wire 4 preferably is round in cross-section although it may be square, rectangular, D shape or any other shape. In the straight portions 6 of the frame the joined wire segments are disposed, relative to the tubular configuration of the frame, circumferentially thereof. Wire 4 abuts itself only at the straight portions 6 and 11. It does not cross itself at any point. Accordingly, the frame wall forming the stent has a thickness equal to the diameter of wire 4. The bridging sections or connecting members 11 extend longitudinally with respect to the longitudinal axis of the stent.

The tubular body portion made up of spaced segments 9 comprises a mesh formed by the winding of wire 4, the mesh comprising a plurality of interconnected cells 7 of a polygonal configuration when viewed in plan, providing straight sides to form the aforementioned straight portions 6 and spaced cell segments 9. The polygonal cells 7 preferably are of a hexagonal configuration and are closed, which readily provides expansion and rigidity characteristics desirable in the structure and operation of the stent. Preferably, the stent comprises 6 of the polygonal cells 7 circumferentially and an even number of the polygonal cells along its length, thereby facilitating formation of the stent by the single wire 4 in the pattern shown in FIG. 2.

The stents of this invention may have disposed thereon an elastomeric or textile sleeve (not shown) such as PET, PTFE, silk, polyurethanes or polyesters for example, which is expandable on the stent as the stent expands to its enlarged configuration. The sleeves may include drugs. The sleeved stent may have added benefit in certain circumstances and thus is considered to be within the scope of the present invention.

The stent wire is preferably made of an alloy of nickel and titanium which provides the stent with a thermal memory. The unique characteristics of such alloys which are generally known as "Nitinol" is that they have thermally triggered shape memories which allows the stent to be constructed in the aforesaid first condition, i.e., expanded and the alloy to be cooled and thereby softened compressing to a second condition, i.e., smaller for loading into a catheter in a relatively compressed state and to regain the memorized enlarged shape when warmed to a selected temperature such as human body temperature. The two interchangeable shapes sizes are possible because of the two different crystalline structures which exist in such alloys at different temperatures.

Accordingly, as is known in the art, when stents of the type described herein are subjected to a temperature at or less than the transition temperature of the alloy, the relatively rigid stent changes to a second condition in which it is relatively compressible. In such a condition the stent may be compressed easily to a small diameter which is conveniently delivered by means of a catheter for implanting. The stent following implantation upon reaching a higher temperature such as body temperature then self-expands to its memorized larger shape.

Of course, the stents of this invention may be made of other materials such as stainless steel to be balloon expandable or the like as known in the art. Polymeric materials may also be used. Composites of Nitinol with other metals such as chrome or nitinol cored wire cored with alloys such as tantalum may be used.

Figure 4:
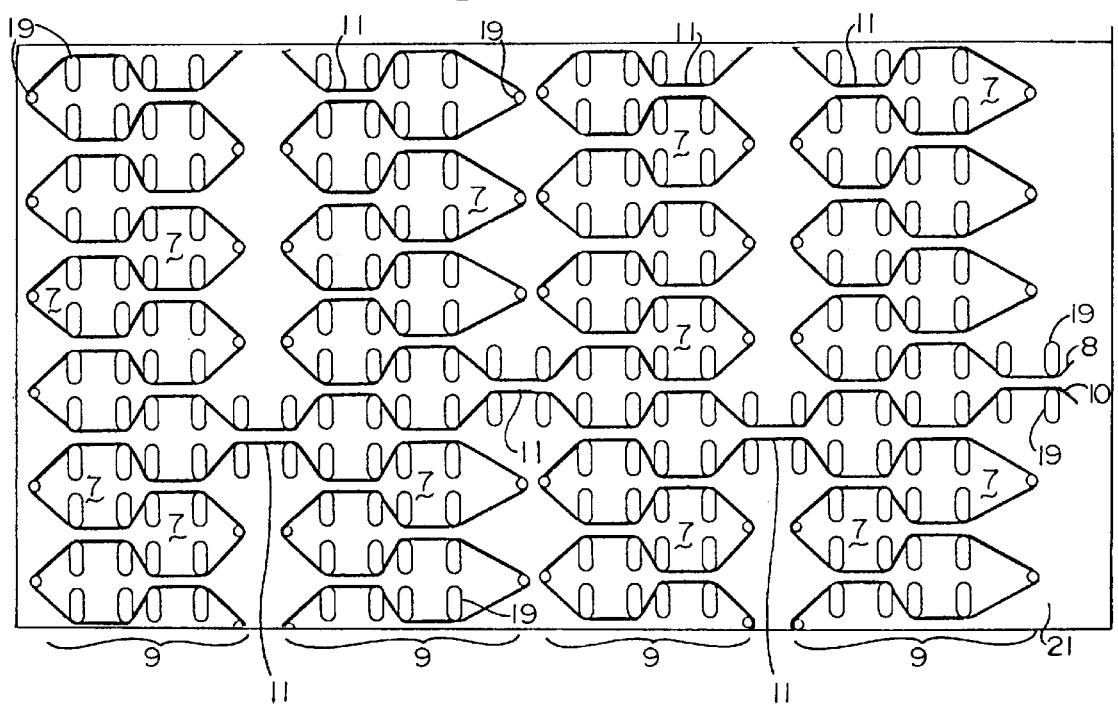
FIG. 4 is a planar view similar to FIG. 2 showing the wire winding patterns for preparing a stent embodiment having a single bridge section between stent segments, the bridge section being parallel to the longitudinal axis of the stent.

FIG. 4 shows the winding pattern for forming a stent similar to that of FIGS. 1–3 but having only one bridging section or connecting member 11 between cell segments 9. Only a single wire is used in this wire winding pattern and the connecting members are parallel to the longitudinal axis of the stent.

Figure 5:
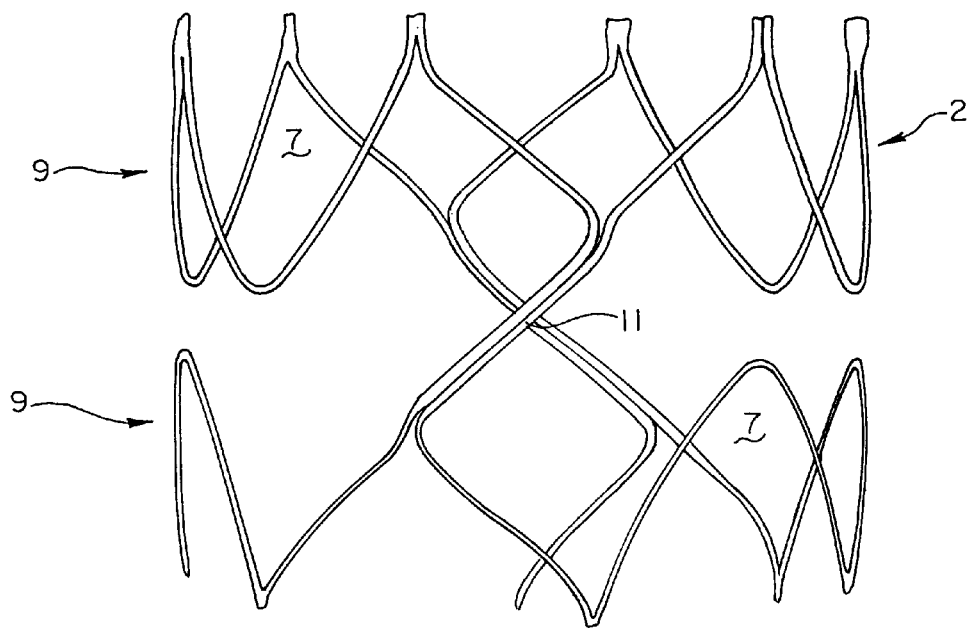
FIG. 5 is a close-up detail view of a portion of a stent embodiment having a single bridge section between stent segments, the bridging sections being at an angle with respect to the longitudinal axis of the stent.
Figure 6:
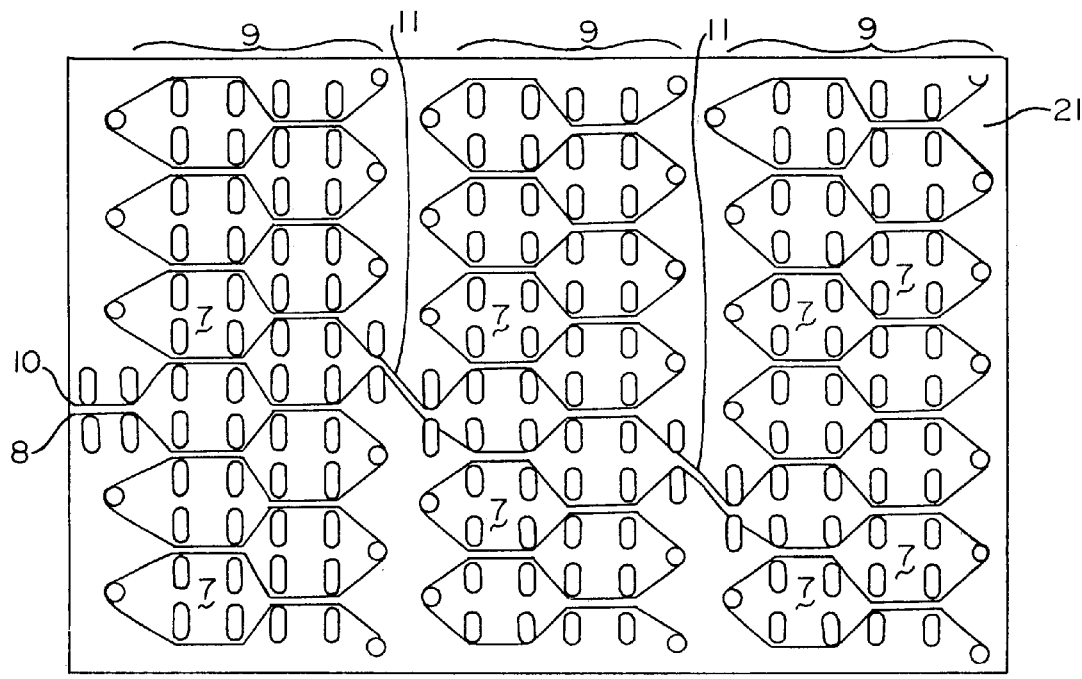
FIG. 6 is a planar view similar to FIGS. 2 and 4 showing the wire winding pattern for preparing a stent embodiment as shown in FIG. 5.

FIG. 5 and 6 shown an embodiment 2 in which the single connecting member 11 between adjacent segments 9 is angularly positioned with respect to the longitudinal axis of the stent. FIG. 5 shows a portion of the stent including the single angled connector between stent segments. FIG. 6 is the winding pattern for this embodiment.

Figure 7:
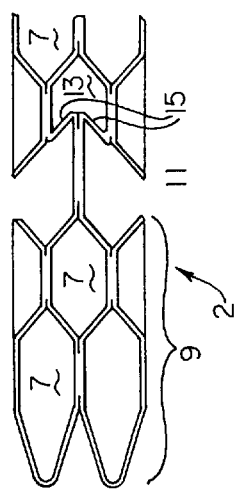
FIG. 7 is a modified showing of a single bridge arrangement for minimizing shortening of the stent during compression.

FIG. 7 shows another alternative stent design 2 with a single bridge connector member 11. It consists of a single wire multiple segment hexagonal cell stent having the ability to provide minimal shortening in overall length during compression to a smaller diameter for delivery. In this design the wire configuration of hexagonal shaped cells 7 emanating from segment 9 join a hexagonal cell 13 having a reverse direction 15 for two sides of the cell to allow the cell to absorb the opposite cell's elongation. This inversion is only necessary at the junction points of connector member connections of the segments. The inversion arrangement may be used with other cell geometric shapes.

Figure 8:
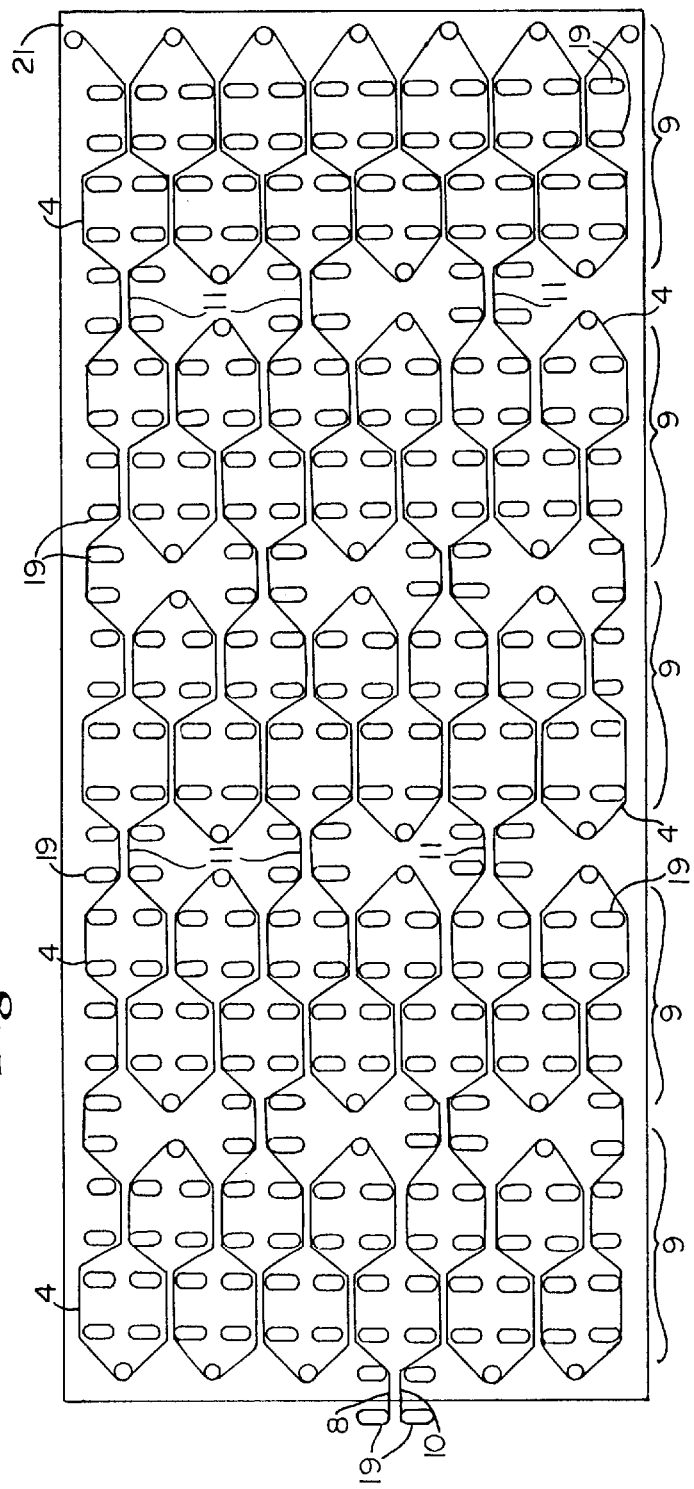
FIG. 8 is a planar view similar to FIGS. 2, 4 and 6 showing the wire winding pattern for preparing a stent having three bridging sections between cell segments.

Referring now to FIG. 8, the wire winding pattern for preparing a stent having three bridge connector members 11 between each of segments 9 is shown. The same members are used to indicate elements which are similar to those of FIGS. 2 and 4.

Figure 9:
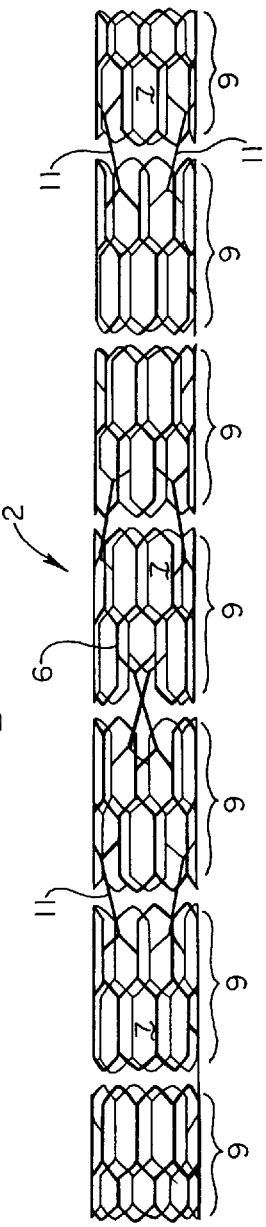
FIG. 9 is a view of an embodiment of a stent having two bridging sections between cell segments, the sections being angularly positioned with respect to each other and with respect to the longitudinal axis of the stent.
Figure 10:
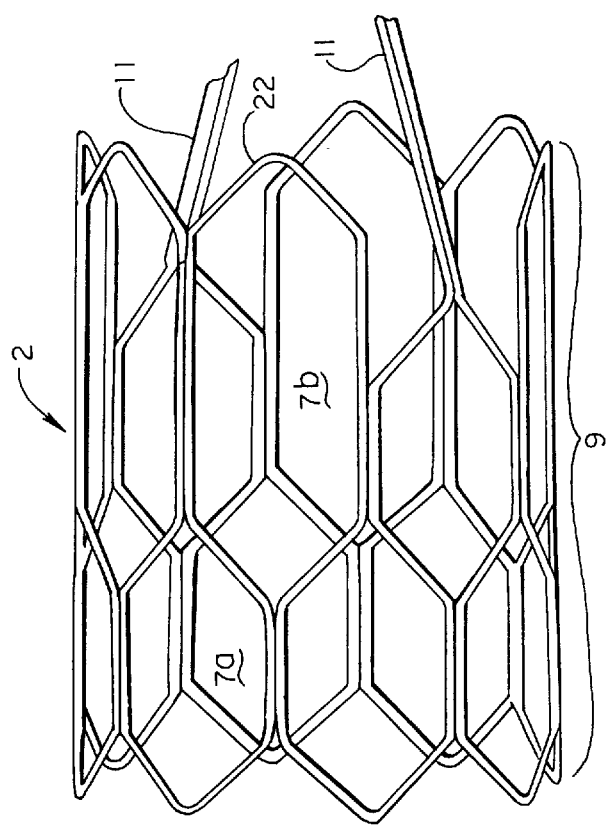
FIG. 10 is a close-up detail view of a portion of the two bridge stent arrangement of FIG. 9 wherein the cell segments are off set with respect to adjacent segments and the bridging sections are at an angle with respect to the longitudinal axis of the stent.
Figure 11:
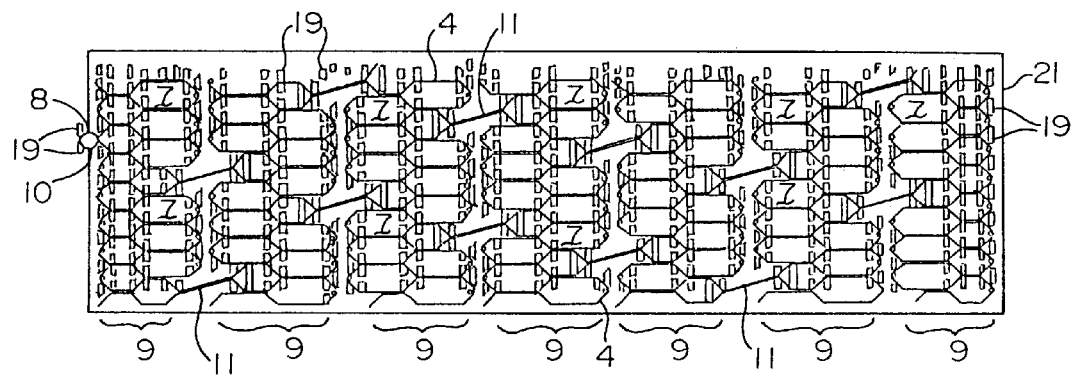
FIG. 11 is a planar view similar to FIGS. 2, 4, 6 and 8 showing the wire winding pattern for preparing the stent of FIGS. 9 and 10.

Another particularly preferred embodiment is shown in FIGS. 9, 10 and 11 wherein the bridging connector members 11 are two in number between segments 9 and are angularly positioned with respect to each other and with respect to the longitudinal axis of the stent. The various size cells 7a and 7b making up each of the cell segments 9, the segments being offset with respect to each other such that the adjacent points 22 of the segments do not contact each other when the stent is bent as in flexing it to move around bends in the vasculature. The same numbers are used to indicate elements similar to those of FIG. 1. FIG. 10 shows a close-up detail of the connectors 11 in a portion of the stent shown in FIG. 9. FIG. 11, similar to FIGS. 2, 4, 6 and 8, show the wire winding pattern to be used in preparing the stent.

Figure 12:
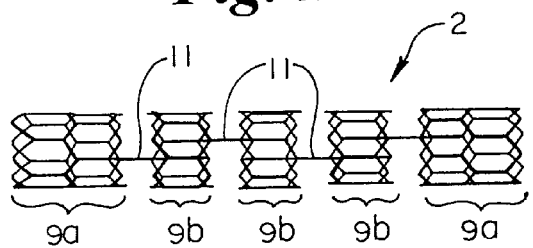
FIG. 12 is a view of another stent embodiment having bridging sections extending between adjacent segments of the stent, successive bridging sections being displaced or staggered circumferentially with respect to each other.
Figure 13:
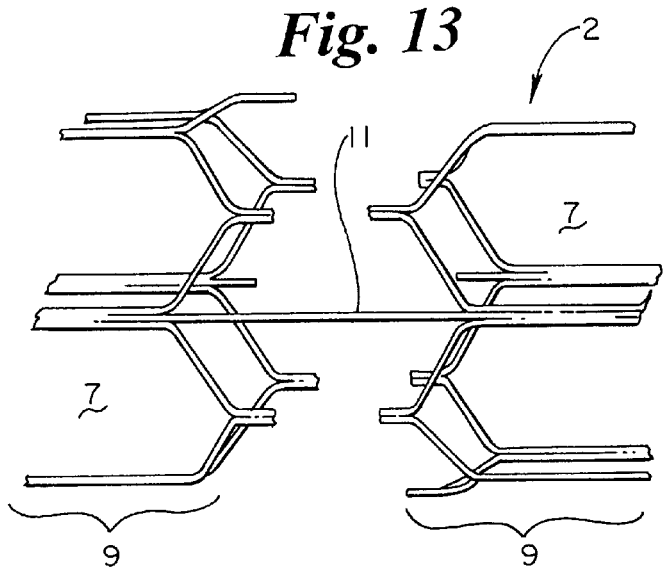
FIG. 13 is a close-up detail view of a portion of the stent of FIG. 12.

The embodiment of FIGS. 12 and 13 differs of the preceding embodiments in that a plurality of wires are used to form the stent. In this embodiment each segment 9 is formed of a individual wire, the end segments 9a being two cells in length while the internal segments 9b are only one cell in length. Connector members 11 extend between adjacent segments 9 and are interconnected as shown in the Figures. This embodiment includes a staggered single wire bridge arrangement between segments.

Figure 14:
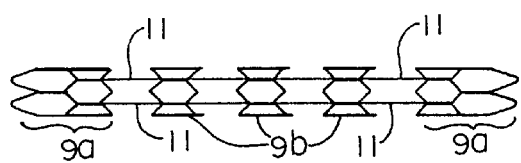
FIG. 14 is a showing of a stent similar to that of FIGS. 12 and 13 except that the bridging sections (two) extend continuously through the length of the stent.

The embodiment of FIG. 14 is similar in most respects to that of FIGS. 12 and 13 except that connector member 11 extends continuously through the longitudinal length of the stent. The two connector members 11 are connected substantially 180° apart. Optionally, only one continuous connector member may be included.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent comprised of a tube form body having a body wall structure of a geometric pattern of cells defined by wire extending throughout the body and defining the cell pattern as a plurality of spaced sections of interconnected cells which in plan view are of polygonal configuration, one or more of the plurality of adjacent spaced sections being defined by at least two rows of cells circumferentially distributed about the tube, adjacent spaced sections being connected to each other by one or more straight connector sections of the wire.

2. The stent of claim 1 wherein the straight sections are comprised of at least one pair of adjoining wires.

3. The stent of claim 1 including two connecting straight sections of the wire, the two being circumferentially spaced apart by about 180°.

4. The stent of claim 1 including three connecting straight sections of the wire, the three being circumferentially spaced apart by about 120°.

5. The stent of claim 1 in which the wire is of a nitinol alloy.

6. The stent of claim 1 wherein the straight connector sections are disposed at an oblique angle relative to the longitudinal axis of the stent.

7. The stent of claim 1 including a covering sleeve.

8. The stent of claim 1 wherein the wire connecting the spaced sections extends continuously throughout the longitudinal length of the stent.

9. The stent of claim 8 including a plurality of continuous connecting wires.

10. The stent of claim 1 in which the cells are of a hexagonal configuration.

11. The stent of claim 10 in which at least some of the cells include two adjacent inverted sides which receive a connecting wire.

12. In a stent comprising a wire skeletal frame, said frame being adapted to assume a first condition in which said frame is expanded, relatively rigid, and substantially tubular in configuration, and being further adapted to assume a second condition in which said frame is flexible, of reduced stress, and collapsible, said wire frame comprised of a metallic compound of nickel and titanium, said compound in said second condition indefinitely retaining said flexibility and said reduced stress and retaining memory of said first condition, said wire frame upon heating to a selected temperature, assuming said first condition in which said frame is greatly expanded relative to said second condition and assuming said rigidity, such that in said second condition walls of said frame are adapted to be positioned in their collapsed disposition, and further adapted to be dispositioned against each other to form a stent diameter substantially equal to the combined thickness of the frame walls in abutting engagement with each other, and further adapted to be configured between said expanded disposition and said walls abutting disposition, said frame in said second condition being substantially devoid of bias therein urging said frame to assume said first configuration when exposed to the selected temperature, said skeletal frame comprising wire, round in cross-section, said frame including straight axially-extending portions of said wire joined together along the lengths of said straight axially-extending portions and circumferentially side by side, wherein in said substantially tubular configuration said frame includes a substantially tubular body portion, the improvement comprising said body portion being defined by a plurality of spaced sections each of which is comprised of a group cells which in plan view are of polygonal configuration, one or more of the plurality of adjacent spaced sections being defined by at least two rows of cells circumferentially distributed about the tube, adjacent spaced sections connected to each other by one or more straight connector sections of wire.

13. The stent of claim 12 in which the selected temperature is normal human body temperature, whereby the frame is adapted to assume the first configuration automatically upon exposure to human body temperature.

14. The stent of claim 12 in which the cells are of a hexagonal configuration.

15. The stent of claim 12 including two connecting pairs of straight sections of the wire, the two pairs being circumferentially spaced apart by about 180°.

16. The stent of claim 12 including three connecting pairs of straight sections of the wire, the three pairs being circumferentially spaced apart by about 120°.

17. The stent of claim 12 wherein the straight sections are comprised of at least one pair of adjoining wires.

18. The stent of claim 12 where the straight connector sections are disposed at an oblique angle relative to the longitudinal axis of the stent.

19. The stent of claim 12 including a covering sleeve.

20. The stent of claim 1 where the straight connector sections of wire are longitudinally aligned with the longitudinal axis of the stent.

21. The stent of claim 1 wherein at least some of the spaced sections are formed of a plurality of cells, the cells interconnected longitudinally as well as circumferentially.

22. The stent of claim 1 wherein at least some of the spaced sections are formed of a plurality of cells which are only interconnected circumferentially.

23. The stent of claim 12 the straight connector sections of wire are longitudinally aligned with the longitudinal axis of the stent.

* * * * *